US009427509B2

(12) United States Patent
Vodermayer et al.

(10) Patent No.: US 9,427,509 B2
(45) Date of Patent: Aug. 30, 2016

(54) TRANSFER ASSEMBLY

(75) Inventors: Bernhard Vodermayer, Gilching (DE); Thomas Schmid, Gilching (DE)

(73) Assignee: DEUTSCHES ZENTRUM FUER LUFT-UND RAUMFAHRT E.V., Cologne (DE)

( * ) Notice: Subject to any disclaimer, the term of this patent is extended or adjusted under 35 U.S.C. 154(b) by 1025 days.

(21) Appl. No.: 11/879,160

(22) Filed: Jul. 16, 2007

(65) Prior Publication Data

US 2008/0027293 A1 Jan. 31, 2008

(30) Foreign Application Priority Data

Jul. 27, 2006 (DE) .................. 10 2006 035 547

(51) Int. Cl.
*A61N 1/378* (2006.01)
*A61N 1/372* (2006.01)
*A61M 1/12* (2006.01)

(52) U.S. Cl.
CPC ............ *A61M 1/127* (2013.01); *A61N 1/3787* (2013.01); *A61N 1/37223* (2013.01); *A61M 2205/3507* (2013.01)

(58) Field of Classification Search
USPC ............................................... 607/29–33, 61
See application file for complete search history.

(56) References Cited

U.S. PATENT DOCUMENTS

| 4,550,731 | A | 11/1985 | Batina et al. |
| 5,314,453 | A | 5/1994 | Jeutter |
| 6,239,724 | B1* | 5/2001 | Doron et al. ............ 340/870.28 |
| 6,273,904 | B1* | 8/2001 | Chen et al. ..................... 607/88 |
| 6,400,991 | B1* | 6/2002 | Kung ............................... 607/61 |
| 6,430,444 | B1* | 8/2002 | Borza ............................. 607/61 |
| 7,103,698 | B2* | 9/2006 | Zhang et al. ................. 710/303 |
| 7,174,201 | B2* | 2/2007 | Govari et al. ................ 600/424 |
| 2004/0106963 | A1 | 6/2004 | Tsukamoto et al. ............ 607/33 |
| 2005/0131486 | A1 | 6/2005 | Boveja et al. |

FOREIGN PATENT DOCUMENTS

WO    WO 2004/021876    3/2004

* cited by examiner

*Primary Examiner* — Allen Porter, Jr.
(74) *Attorney, Agent, or Firm* — Ohlandt, Greeley, Ruggiero & Perle, LLP

(57) ABSTRACT

A transfer assembly comprising an intracorporeal transfer coil of an implant, and an extracorporeal transfer coil of an extracorporeal supply unit. The transfer coil of the implant has permanently associated therewith a transmitting element. The transfer coil of the supply unit has permanently associated therewith at least one receiving element. Further, the supply unit comprises an evaluation module connected with the receiving element and issuing a locating signal depending on an offset and/or a direction of offset of the transmitting element relative to the receiving element.

15 Claims, 3 Drawing Sheets

TRANSFER ASSEMBLY

BACKGROUND OF THE INVENTION

1. Field of the Invention

The present invention relates to a transfer assembly comprising an intracorporeal transfer coil of an implant and an extracorporeal transfer coil of an extracorporeal supply means.

2. Description of Related Art

Medical implants for supporting the heart and organ activities, for example, can generally be partially or fully implanted. Partially implanted implants comprise lines for energy supply and data transfer, said lines extending through the skin to an extracorporeal transfer means. The line lead-through devices in the skin are a common source of infection. Further, the patient is restricted in his freedom of movement by the line lead-through devices.

As an alternative to partially implanted implants, fully implanted implants are provided. In particular implants performing mechanical work, for example blood pumps, have an energy requirement of 2 to 20 watts. This required energy can be made available by the implant's own accumulator for a short period of a few hours at the most. For operating implants with an energy requirement of more than 1 to 2 watts, a continuous or nearly continuous extracorporeal energy supply is indispensable. The energy supply of such an implant and the data transfer are carried out in a cordless manner through an intracorporeal supply coil of the implant and an extracorporeal transfer coil of the supply means. Energy and data are inductively transferred between the two transfer coils. For data and energy transfer between the supply means and the implant, the two transfer coils are placed one on top of the other such that they overlap each other to the largest extent possible. The extracorporeal supply means is frequently configured as a belt or a pouch and extracts the energy to be transferred to the implant from batteries or the public power supply system.

For obtaining as high an efficiency as possible during energy and data transfer, the two transfer coils must be placed one on top of the other as exactly as possible and must then be correspondingly fixed relative to each other. Said fixing is carried out by gluing the supply means and/or its transfer coil to the skin, for example.

Transfer assemblies are known which are comfortable to be used by a patient and whose supply means and/or transfer coil are not fixed by gluing. For example, the transfer coil of the supply means may be accommodated in a belt which can be easily removed by the patient. However, since the transfer coil of the supply means is not fixed to the skin by gluing, there is the risk that, during the inductive transfer, the belt and the transfer coil of the supply means shift when the patient moves, and therefore the electromagnetic coupling and thus the efficiency of the energy transfer and the data transfer are reduced.

Another problem is the exact placing and alignment of the extracorporeal transfer coil of the supply means over or on top of the intracorporeal transfer coil of the implant. In practice, the position of the intracorporeal transfer coil of the implant must be located by palpating. If it is not possible to locate the transfer coil of the implant by palpating, a corresponding marking is to be placed at the respective place on the skin of the patient.

In US 2004/0106963 A1 a transfer assembly for an implant is described, where on the implant side a ferromagnetic tissue mat and, alternatively, a mat comprising a plurality of microchips is provided. The signals from the ferromagnetic mat cannot be modulated. Further, a direction of offset cannot be clearly determined from the point of view of the supply means. Although the alternative implant-side mat made of microchips theoretically allows a direction of offset to be determined, said direction of offset can be determined only from the point of view of the implant. A correction indication could therefore only be supplied from the implant side. Indication of the direction of offset at the extracorporeal supply means would require knowledge of the rotatory position of the supply means.

From the printed publication WO 2004/021876 A1 a transfer assembly is known which comprises a single coil both at the implant side and at an extracorporeal location for determining the amount of offset.

SUMMARY OF THE INVENTION

It is an object of the present invention to provide a simple transfer assembly which allows for an improved check of the alignment of the transfer coil of the implant with the transfer coil of the supply means.

The transfer assembly according to the invention comprises a locating transmitter permanently associated with the transfer coil of the implant, and a locating receiver permanently associated with the transfer coil of the supply means. Further, an evaluating module associated with the supply means is provided, which evaluating module is connected with the receiver and issues a locating signal depending on the offset and the direction of offset between the transmitter and the receiver.

The optical transmitting element can be arranged exactly in the center of the intracorporeal transfer coil of the implant, for example. For determining the direction of offset beyond the offset, at least three receiving elements are provided, which are arranged relative to each other in the form of an equilateral triangle, for example. Besides the approximate offset, the approximate direction of offset can be determined.

The transmitter and the receiver operate with the same type of waves, for example light waves, electromagnetic fields, radio waves or acoustic waves. The evaluating module connected with the receiver is capable of determining, from the intensity of the signal coming from the transmitter, the offset, i.e. the distance and the direction of offset, i.e. the solid or plane angle of offset, of the transmitter relative to the receiver, and of issuing a corresponding locating signal.

The locating signal can be issued acoustically, optically or in any other way, and enables the patient to correct the position of the transfer coil of the supply means such that the transfer coil of the supply means is to a large extent congruent with the transfer coil of the implant. Since it is possible to check the offset of the transfer coil of the implant relative to the transfer coil of the supply means, the offset can be continuously checked and kept at a low level. Thus the efficiency and/or the performance of the transfer, in particular the energy transfer between the supply means and the implant, are improved. This, in turn, reduces the heat development, improves the service life of the components involved, and, in the case of data transfer, improves the quality of the data transfer.

The locating signal may also be used for automatically, i.e. with the aid of corresponding actuating motors, realigning the transfer coil of the supply means in an optimum manner to the transfer coil of the implant.

The transfer coils serve for energy transfer purposes, but may additionally or alternatively be used for data transfer between the supply means and the implant.

Preferably, a transmitting element of the transmitter is configured as a coil, and the receiver comprises a magnetic field receiving element. The receiving element may also be configured as a coil or as a Hall sensor. The transmitting element may be the transfer coil of the implant, but may also be a separate transmitting element coil. The transmitting element or elements are connected with the receiving element or elements via an electromagnetic field. The intensity of the field detected by the receiving element or elements is a measure of the distance of the receiving element configured as a coil. Preferably, the receiving coil has a considerably smaller circumference than the transfer coil of the supply means and/or the transfer coil of the implant. This allows the alignment of the two transfer coils relative to each other to be determined in a considerably more exact manner.

As an alternative to an inductive configuration of the receiving element and the transmitting element, said elements may also be optical components. The transmitting element is then a light source emitting light in the visible and/or invisible range. The receiving element is an optical receiving element receiving and quantifying the light emitted by the transmitting element. Infrared light is particularly suitable since the skin and the subcutaneous tissue show a relatively low absorptivity with regard to infrared light. In particular a photo transistor or a photo diode can be used as a receiving element.

According to another preferred embodiment, the transmitter comprises a plurality of transmitting elements whose transmitted signals differ from each other. For example, light emitting diodes of different colors and/or wavelengths can be used as transmitting elements. Further, the receiving element must be capable of differentiating the radiation emitted by the transmitting elements, i.e. receiving said radiation in a wavelength-selective manner when optical transmitting elements are used. If a single receiving element generating a spectrum is employed for this purpose, the direction of offset can be determined in this manner with a single receiving element. If at least two wavelength-selective receiving elements are used, the rotatory position of the transfer coil of the implant relative to the transfer coil of the supply means can also be determined.

The signals received by the receiving elements are evaluated in a microcomputer and/or a microcontroller, and a corresponding locating signal is issued by the microcomputer and/or the microcontroller.

Since data are frequently exchanged between the implant and the supply means via infrared transmitting elements and infrared receiving elements, the optical variant may be realized with only a small extra effort or no extra effort at all regarding the hardware.

For preventing disturbances by external light sources, the optical signals may be modulated, they may be pulsed for example. Its pulsating frequency allows the optical transmitting element to be clearly identified on the receiver side and to be differentiated from the light coming from other light sources. If the transmitting element of the device involved also acts as a transmitting element for the optical data transfer between the implant and the supply means, the offset recognition is not activated continuously but in a clocked manner, for example.

BRIEF DESCRIPTION OF THE DRAWINGS

Several embodiments of the invention will now be described in greater detail with reference to the drawings in which.

DETAILED DESCRIPTION OF PREFERRED EMBODIMENTS OF THE INVENTION

Figure 1:
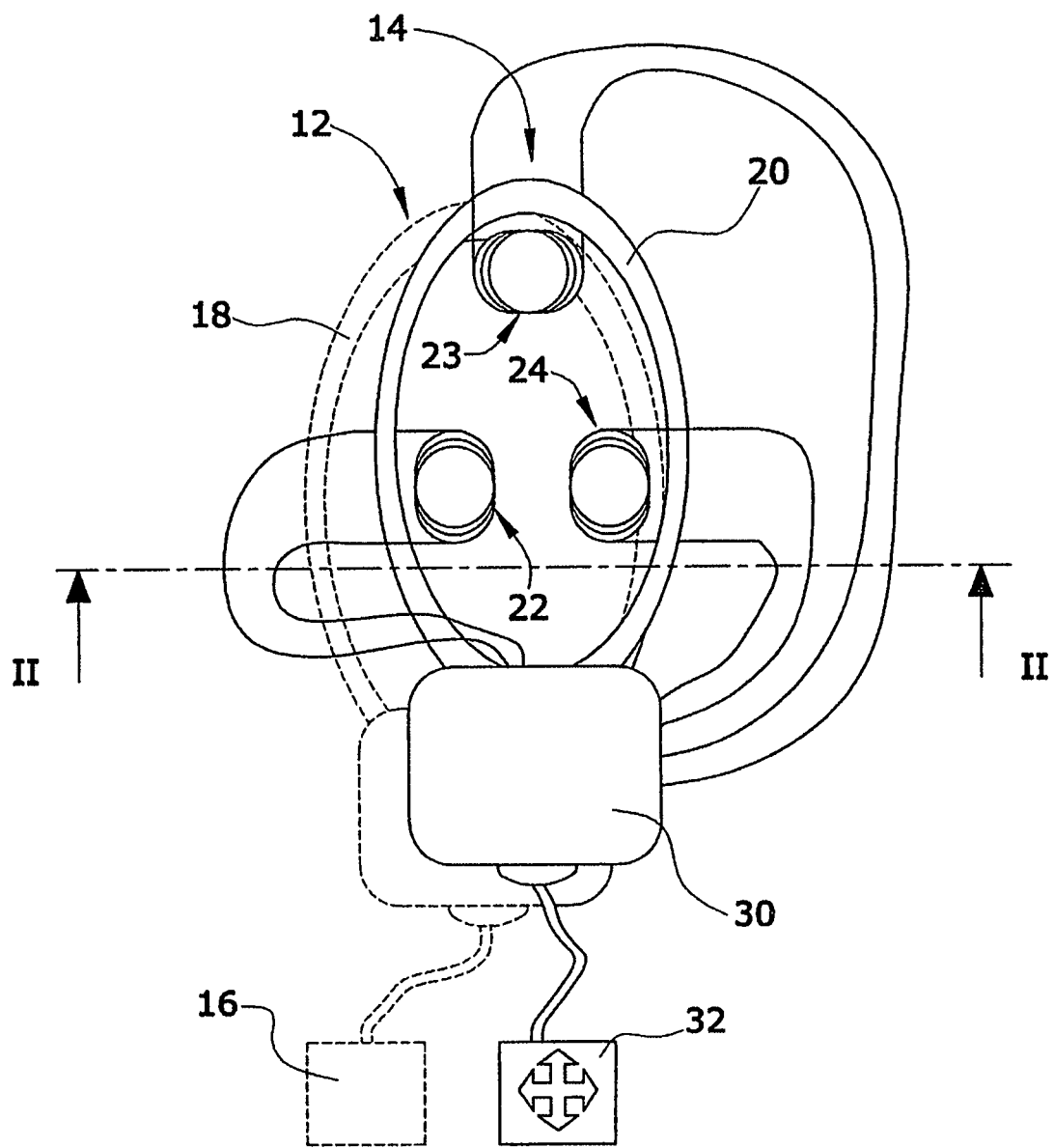
FIG. 1 shows a schematic diagram of a transfer assembly comprising electromagnetic transmitting and receiving elements.

FIG. 1 shows a first embodiment of a transfer assembly 10. The transfer assembly 10 comprises an intracorporeal implant 12 represented by a dashed line, and an extracorporeal supply means 14. The implant 12 is a blood pump for supporting a patient's heart activity, for example, and comprises a pumping means 16. The pumping means 16 usually operates continuously and has an energy requirement ranging from several watts to 20 watts. The implant 12 is a so-called fully implanted implant, i.e. the implant 12 has no physical connection with the outside of the body.

The electrical energy required for operating the blood pump 16 must therefore be transferred in a cordless manner. The transfer is performed via an implant 12 transfer coil 18 which is implanted immediately beneath the skin, and an extracorporeal transfer coil 20 of the extracorporeal supply means 14. In the transfer coil 20 of the supply means 14 small coils configured as receiving elements 22,23,24 are arranged which define inductive receiving elements for an alternating magnetic field.

The transfer coil 18 of the implant 12 defines a transmitting element acting as the transmitter with respect to the receiver and/or the receiving elements 22 to 24 of the supply means 14.

If an optimum coupling exists between the two transfer coils 18,20, approximately the same induced voltage and/or the same induced current are measured in the receiving elements 22 to 24 in the course of an alternating field generated for a short time in the transfer coil 18 of the implant 12.

The measurement of the induced current and/or the induced voltage of the receiving elements 22,23,24 is performed in an evaluation module 30 which is electrically connected with the three receiving elements 22,23,24. Depending on the measured offset and the measured direction of offset between the transmitting element and the receiving elements 22,23,24, the evaluation module 30 feeds a corresponding locating signal to an optical display unit 32. The optical locating display unit 32 is associated with the supply means 14 and can be easily read by the patient. This allows the patient to optimally align the extracorporeal transfer coil 20 of the supply means 14 with the intracorporeal transfer coil 18 of the implant 12.

Figure 2:
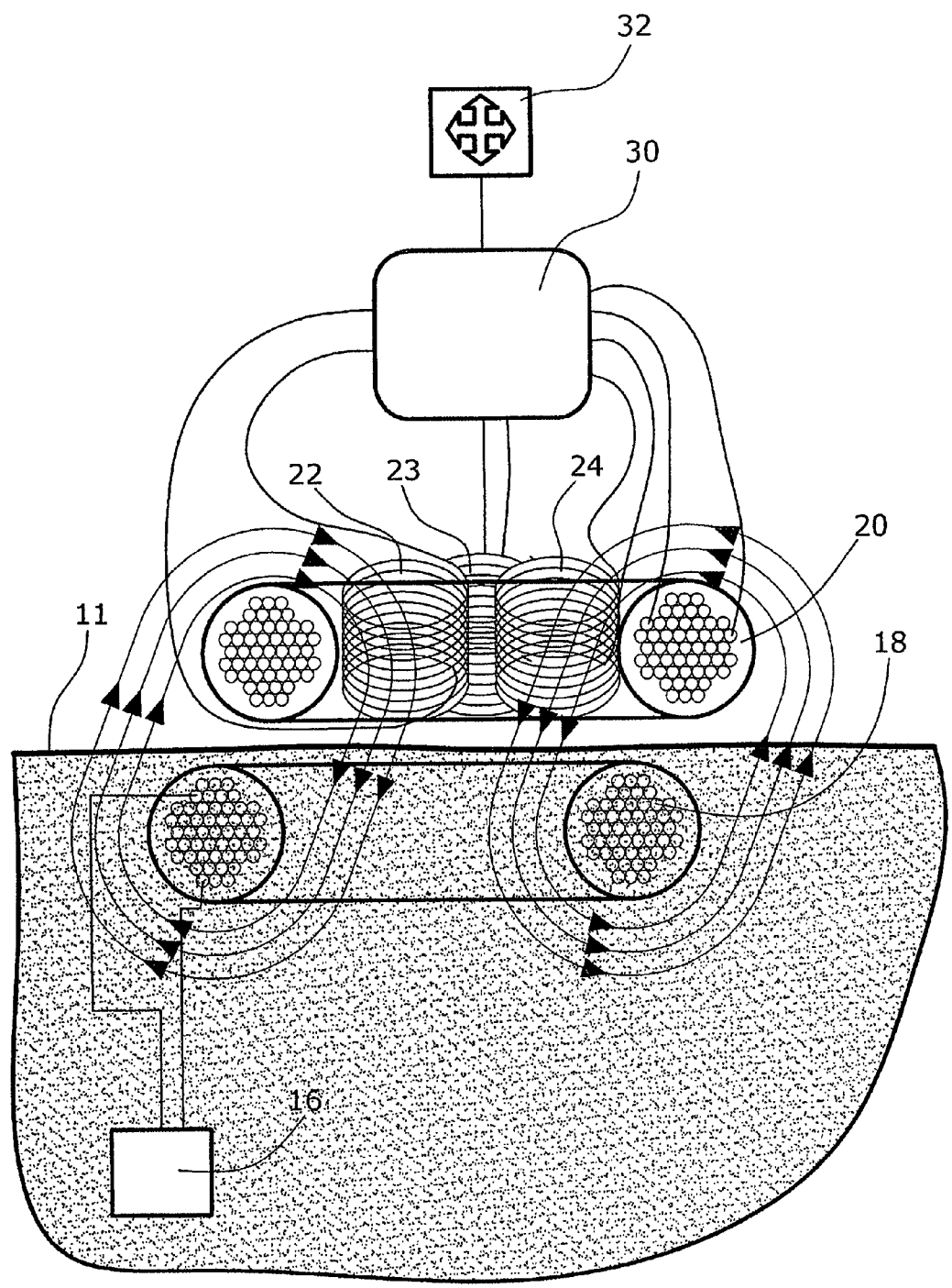
FIG. 2 shows a cross-sectional view of the transfer assembly of FIG. 1.

As can be seen in FIG. 2, the transfer coil 18 of the implant 12 is arranged subcutaneously, i.e. immediately beneath the skin 11.

Figure 3:
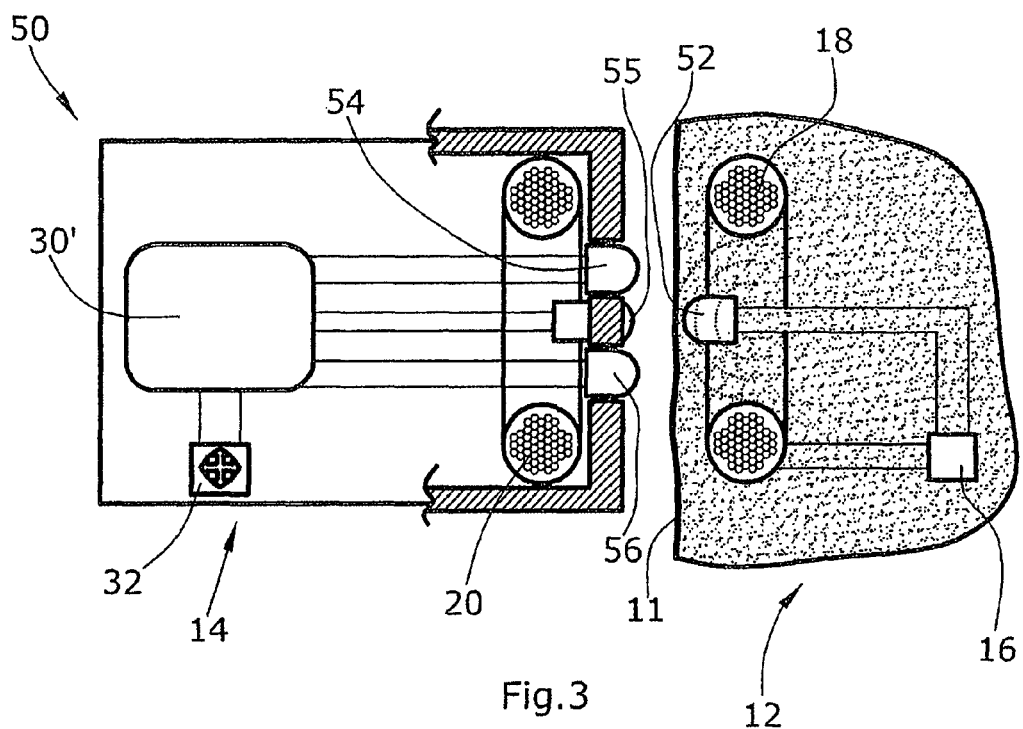
FIG. 3 shows a second embodiment of a transfer assembly comprising optical transmitting and receiving elements.

FIG. 3 shows a second embodiment of a transfer assembly 50, wherein the transmitter is defined by an optical transmitting element 52, and the receiver is defined by three optical receiving elements 54,55,56.

The transmitting element 52 is an infrared diode which is operated in a pulsed manner. The receiving elements 54,55, 56 are photo diodes comprising infrared filters. In an evaluation module 30' the signals coming from the optical receiving elements 54,55,56 are filtered by a band-pass filter whose filtering frequency is the pulse frequency at which the transmitting element 52 is chopped.

The evaluation of the infrared light intensity emitted by the transmitting element 52 and received by the receiving elements 54,55,56 enables the evaluation module 30' to send a signal to the locating display 32, said signal furnishing information both on the direction of offset and on the amount of offset between the transfer coil 20 of the supply means 14 and the transfer coil 18 of the implant 12.

Figure 4:
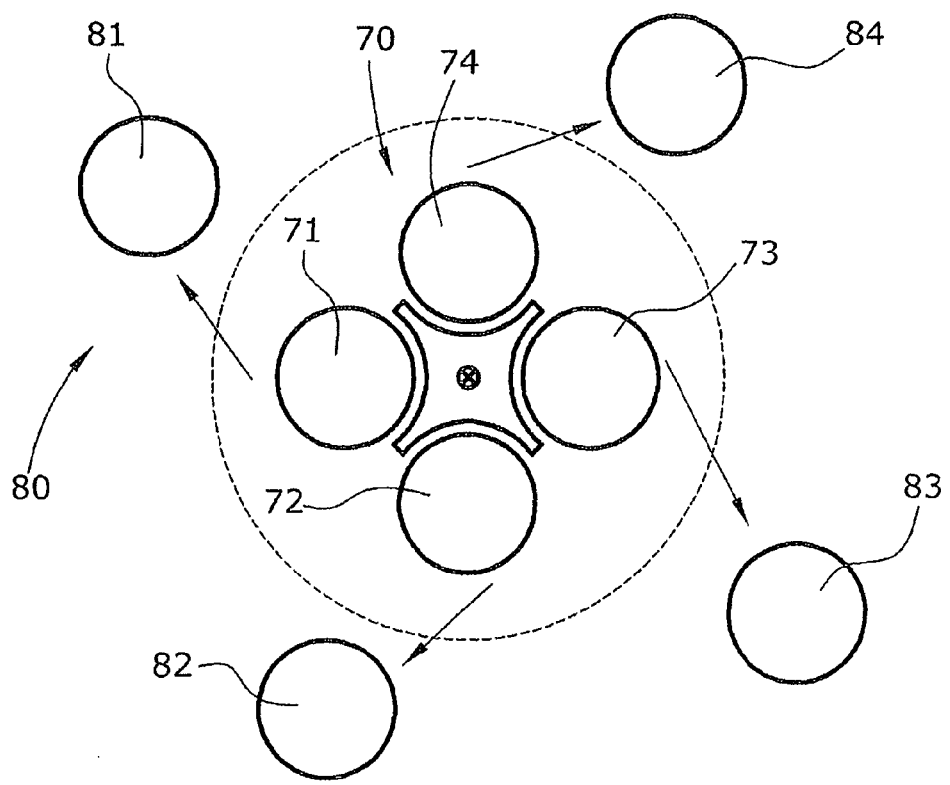
FIG. 4 shows the arrangement of optical transmitting and receiving elements of a third embodiment of a transfer assembly.

FIG. 4 shows an alternative embodiment of a transmitter 70 and a receiver 80 defined by receiving elements 81 to 84. Transmitting elements 71 to 74 are light emitting diodes of different colors and/or different wavelengths. The same applies to the receiving elements 81 to 84 which are selectively sensitive to the radiation of a corresponding transmitting element 71 to 74. In this manner, a corresponding evaluation further allows the rotatory position of the transfer coil 20 of the supply means 14 relative to the transfer coil 18 of the implant 12 to be determined, to be issued as a locating signal, and to be corrected, if necessary.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

What is claimed is:

1. A transfer assembly comprising:
    an intracorporeal transfer coil of an implant and an extracorporeal transfer coil of an extracorporeal supply device,
    wherein said intracorporeal transfer coil is a single locating transmitter;
    a receiver of said extracorporeal supply device comprising a plurality of receiving elements; and
    an evaluation module associated with said extracorporeal supply device and connected with said receiver, said evaluation module issuing, depending on an angle of offset between said intracorporeal transfer coil and said plurality of receiving elements, a locating signal indicating the angle of offset, wherein said evaluation module determines said angle of offset based on an induced current and/or induced voltage measured by each of said plurality of receiving elements.

2. The transfer assembly according to claim 1, wherein the plurality of receiving elements comprises magnetic field receiving elements.

3. The transfer assembly according to claim 1, wherein the receiving elements are configured as Hall sensors.

4. The transfer assembly according to claim 1, wherein the receiving elements are configured as coils.

5. The transfer assembly according to claim 1, wherein the locating transmitter is configured as an optical transmitting element, and the receiver comprises optical receiving elements.

6. The transfer assembly according to claim 5, wherein the optical transmitting element is an infrared transmitting element.

7. The transfer assembly according to claim 1, wherein said locating signal indicating the angle of offset is based on a rotatory position of said extracorporeal transfer coil.

8. A transfer assembly comprising:
    an implant having an intracorporeal transfer coil and an optical transmitting element arranged in a center of said intracorporeal transfer coil;
    an extracorporeal supply device having an extracorporeal transfer coil, said extracorporeal transfer coil having a plurality of optical receiving elements; and
    an evaluation module associated with said extracorporeal supply device and connected with said plurality of optical receiving elements, said evaluation module issuing, depending on an angle of offset between said optical transmitter element and said plurality of optical receiving elements, a locating signal indicating the angle of offset.

9. The transfer assembly according to claim 8, wherein the optical transmitter element is an infrared transmitting element.

10. A transfer assembly comprising:
    an implant having an intracorporeal transfer coil, said intracorporeal transfer coil having an optical transmitter element;
    an extracorporeal supply device having an extracorporeal transfer coil, said extracorporeal transfer coil having a plurality of optical receiving elements; and
    an evaluation module associated with said extracorporeal supply device and connected with said plurality of optical receiving elements, said evaluation module issuing, depending on a direction of offset between said optical transmitter element and said plurality of optical receiving elements, a locating signal indicating the direction of offset, wherein the optical transmitter element comprises a plurality of optical transmitter elements whose transmitted signals differ from each other.

11. A transfer assembly comprising:
    an implant having an intracorporeal transfer coil, said intracorporeal transfer coil having an optical transmitter element;
    an extracorporeal supply device having an extracorporeal transfer coil, said extracorporeal transfer coil having a plurality of optical receiving elements; and
    an evaluation module associated with said extracorporeal supply device and connected with said plurality of optical receiving elements, said evaluation module issuing, depending on a direction of offset between said optical transmitter element and said plurality of optical receiving elements, a locating signal indicating the direction of offset, wherein said locating signal indicating the direction of offset is based on a rotatory position of said extracorporeal transfer coil.

12. A transfer assembly comprising:
    an intracorporeal transfer coil of an implant and an extracorporeal transfer coil of an extracorporeal supply device;
    a transmitter associated with said intracorporeal transfer coil;
    a plurality of receiving elements defining said extracorporeal transfer coil; and
    an evaluation module associated with said extracorporeal supply device and connected with said plurality of receiving elements, said evaluation module issuing, depending on an angle of offset between said transmitter and said plurality of receiving elements, a locating signal indicating the angle of offset, wherein said evaluation module determines said angle of offset based on an induced current and/or induced voltage measured by each of said plurality of receiving elements.

13. The transfer assembly according to claim 12, wherein said locating signal is based on a rotatory position of said extracorporeal transfer coil.

14. The transfer assembly according to claim 12, wherein said transmitter comprises a single transmitter.

15. A transfer assembly comprising:
- an implant having a single intracorporeal transfer coil transmitting a signal;
- an extracorporeal supply device having an extracorporeal transfer coil with a plurality of receiving elements arranged around a circumference for receiving said signal, said circumference of plurality of receiving elements being smaller than said single intracorporeal transfer coil and/or said extracorporeal transfer coil;
- an evaluation module connected with said plurality of receiving elements, said evaluation module determining, based on said signal received at each of said plurality of receiving elements, an angle of offset between said single intracorporeal transfer coil and said plurality of receiving elements, wherein said evaluation module determines said angle of offset based on an induced current and/or induced voltage measured by each of said plurality of receiving elements; and
- a display unit in communication with said evaluation module so as to display a locating signal that is based on said angle of offset.

* * * * *